US012653977B2

(12) United States Patent
Chaudhry

(10) Patent No.: US 12,653,977 B2
(45) Date of Patent: Jun. 16, 2026

(54) ASSEMBLIES AND METHODS FOR DETECTING ACCIDENTAL EXTUBATION OF A TUBE

(71) Applicant: H. LEE MOFFITT CANCER CENTER AND RESEARCH INSTITUTE, INC., Tampa, FL (US)

(72) Inventor: Tariq Chaudhry, Boston, MA (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 383 days.

(21) Appl. No.: 17/276,865

(22) PCT Filed: Sep. 18, 2019

(86) PCT No.: PCT/US2019/051708
§ 371 (c)(1),
(2) Date: Mar. 17, 2021

(87) PCT Pub. No.: WO2020/061178
PCT Pub. Date: Mar. 26, 2020

(65) Prior Publication Data
US 2022/0023562 A1      Jan. 27, 2022

Related U.S. Application Data

(60) Provisional application No. 62/732,862, filed on Sep. 18, 2018.

(51) Int. Cl.
*A61M 16/04*          (2006.01)
*A61B 1/005*          (2006.01)

(52) U.S. Cl.
CPC ......... *A61M 16/0434* (2013.01); *A61B 1/005* (2013.01); *A61M 16/0418* (2014.02); *A61M 2205/583* (2013.01)

(58) Field of Classification Search
CPC ..... A61B 1/00082; A61B 1/005; A61B 1/267; A61J 15/00; A61M 16/0418;
(Continued)

(56) References Cited

U.S. PATENT DOCUMENTS

| | | | | |
|---|---|---|---|---|
| 5,010,892 A | * | 4/1991 | Colvin | A61B 5/1076 |
| | | | | 600/587 |
| 5,033,466 A | * | 7/1991 | Weymuller, Jr. | A61M 16/0459 |
| | | | | 128/207.14 |

(Continued)

FOREIGN PATENT DOCUMENTS

CN          102974014 B        3/2016

OTHER PUBLICATIONS

International Search Report and Written Opinion in PCT/US2019/051708. Mailed Nov. 19, 2019. 7 pages.

*Primary Examiner* — Timothy A Stanis
*Assistant Examiner* — Matthew D Ziegler
(74) *Attorney, Agent, or Firm* — Meunier Carlin & Curfman LLC

(57)          ABSTRACT

Various implementations include an endotracheal tube assembly including an endotracheal tube, an inflatable annular air cuff, an annular slider cuff, an air cuff tubing, and a pointer. The tube includes a visual indicator portion adjacent the proximal end of the endotracheal tube. The inflatable annular air cuff is disposed around the exterior surface of the endotracheal tube and is affixed to the distal end of the endotracheal tube. The annular slider cuff is slidably disposed around the endotracheal tube, and the slider cuff is affixed to the air cuff. The air cuff tubing is coupled to the slider cuff, and the pointer is coupled to the air cuff tubing proximal to the visual indicator portion. Axial movement of the slider cuff causes movement of the pointer relative to the (Continued)

visual indicator portion indicates movement of the endotracheal tube within the trachea during use.

20 Claims, 2 Drawing Sheets

(58) Field of Classification Search
CPC ........ A61M 16/0434; A61M 2205/075; A61M 2205/583
See application file for complete search history.

(56) References Cited

U.S. PATENT DOCUMENTS

| | | | | |
|---|---|---|---|---|
| 5,259,371 | A * | 11/1993 | Tonrey | A61M 16/04 128/207.14 |
| 6,460,540 | B1 * | 10/2002 | Klepper | A61M 16/0463 128/207.14 |
| 9,526,856 | B2 * | 12/2016 | Azagury | A61M 16/0434 |
| 9,770,194 | B2 * | 9/2017 | Azagury | A61B 5/1076 |
| 9,918,618 | B2 | 3/2018 | Molnar | |
| 11,357,953 | B2 * | 6/2022 | Davies | A61M 25/0147 |
| 2002/0096177 | A1 | 7/2002 | Toti et al. | |
| 2014/0109903 | A1 | 4/2014 | Chaudhry et al. | |
| 2015/0096561 | A1 * | 4/2015 | Garrett | A61M 16/0434 128/207.15 |
| 2019/0232007 | A1 | 8/2019 | Chaudhry | |

* cited by examiner

ASSEMBLIES AND METHODS FOR DETECTING ACCIDENTAL EXTUBATION OF A TUBE

CROSS REFERENCE TO RELATED APPLICATIONS

This application is a United States National Phase Patent Application of International Patent Application Number PCT/US2019/051708, filed on Sep. 18, 2019, which claims the benefit of priority to U.S. Provisional Application No. 62/732,862, filed Sep. 18, 2018, which is incorporated by reference herein in its entirety.

BACKGROUND

Accidental extubation of endotracheal tubes occurs in about 10% of all intubated patients, equating to approximately 200,000 events per year. Treatment (re-intubation) can costs around $1,000 per event. Furthermore, re-intubation can lead to patient injury and a prolonged intensive care unit stay, costing the patient an average of $4,000 per day. Previous methods of detecting accidental extubation have included electronic devices (e.g., Sonar-Med) that use sound waves to monitor the movement of endotracheal tubes. While this device is used by some hospitals with proven results, upfront costs and extensive equipment setup have prevented a widespread usage. Thus, there is a need for a device for detecting accidental extubation of endotracheal tubes that is easier to use and more cost effective.

BRIEF SUMMARY

Various implementations include an endotracheal tube assembly. The endotracheal tube assembly includes an endotracheal tube, an inflatable annular air cuff, an annular slider cuff, an air cuff tubing, and a pointer. The endotracheal tube has a tube axis, an exterior surface, a proximal end, and a distal end for inserting into a trachea. The tube further includes a visual indicator portion viewable from the exterior surface. The visual indicator portion is adjacent the proximal end of the endotracheal tube.

The inflatable annular air cuff has a proximal end, a distal end, and inner and outer annular walls that extend between the proximal and distal ends and define an interior of the inflatable air cuff. The air cuff is disposed around the exterior surface of the endotracheal tube such that the distal end of the air cuff is closer than the proximal end of the air cuff to the distal end of the endotracheal tube. The distal end of the air cuff is affixed to the endotracheal tube, and the proximal end of the air cuff defines an opening between the inner and outer annular walls.

The annular slider cuff has a slider axis. The slider cuff defines a first opening, a second opening, and a channel that extends between the first and second openings through the slider cuff. The slider cuff is slidably disposed around the exterior surface of the endotracheal tube such that the slider axis is coaxial with the tube axis. The slider cuff is affixed to the proximal end of the air cuff such that the first opening of the slider cuff is in fluid communication with the opening of the air cuff.

The air cuff tubing has a proximal end, a distal end, and an intermediate portion disposed between the proximal and distal ends of the air cuff. The tubing defines an interior. The distal end of the air cuff tubing is sealingly coupled to the second opening of the slider cuff such that the interior of the air cuff tubing is in fluid communication with the channel of the slider cuff. At least a portion of the intermediate portion of the air cuff tubing is slidably disposed adjacent the exterior surface of the endotracheal tube in a direction parallel to the tube axis.

The pointer is coupled to the intermediate portion of the air cuff tubing. The pointer is disposed in a first axial position relative to the visual indicator portion when the distal end of the endotracheal tube is in an acceptable position within the trachea.

Axial movement of the slider cuff causes movement of the pointer in a direction that is parallel to the tube and slider cuff axes such that the pointer is in a second position that is spaced apart from the first position.

In some implementations, the visual indicator portion includes a plurality of measurement markings disposed in a pattern parallel to the tube axis. In some implementations, the measurement markings are disposed on the exterior surface of the tube.

In some implementations, the distal end of the air cuff is affixed to the endotracheal tube by an adhesive.

In some implementations, the endotracheal tube assembly further includes an air cuff tubing guide defining a channel that extends between a first end and a second end of the air cuff tubing guide. The ends are axially spaced apart along a central axis of the air cuff tubing guide. An external surface of the air cuff tubing guide is coupled to the exterior surface of the endotracheal tube. The central axis of the air cuff tubing guide extends parallel to the tube axis. The air cuff tubing extends through the channel and openings defined by the first and second ends of the air cuff tubing guide. In some implementations, the air cuff tubing guide defines a slot extending between an external surface and an internal surface of the air cuff tubing guide, and the pointer extends from the air cuff tubing through the slot. In some implementations, the air cuff tubing guide includes a plurality of loops coupled to the exterior surface of the endotracheal tube, and the pointer coupled to the air cuff tubing is axially spaced apart from the loops.

In some implementations, the distal end of the endotracheal tube includes a curved, atraumatic edge.

In some implementations, the proximal end of the air cuff tubing is coupled with an air cuff pilot balloon.

BRIEF DESCRIPTION OF DRAWINGS

Example features and implementations are disclosed in the accompanying drawings. However, the present disclosure is not limited to the precise arrangements and instrumentalities shown.

DETAILED DESCRIPTION

Various implementations include an endotracheal tube assembly. The endotracheal tube assembly, according to some implementations, includes an endotracheal tube, an inflatable annular air cuff, an annular slider cuff, an air cuff tubing, and a pointer. The endotracheal tube has a tube axis, an exterior surface, a proximal end, and a distal end for inserting into a trachea. The tube further includes a visual indicator portion that is viewable from the exterior surface. The visual indicator portion is adjacent the proximal end of the endotracheal tube.

The inflatable annular air cuff has a proximal end, a distal end, and inner and outer annular walls that extend between the proximal and distal ends and define an interior of the inflatable air cuff. The air cuff is disposed around the exterior surface of the endotracheal tube such that the distal end of the air cuff is closer than the proximal end of the air cuff to the distal end of the endotracheal tube. The distal end of the air cuff is affixed to the endotracheal tube and the proximal end of the air cuff defines an opening between the inner and outer annular walls.

The annular slider cuff has a slider axis. The slider cuff defines a first opening, a second opening, and a channel that extends between the first and second openings through the slider cuff. The slider cuff is slidably disposed around the exterior surface of the endotracheal tube such that the slider axis is coaxial with the tube axis. The slider cuff is affixed to the proximal end of the air cuff such that the first opening of the slider cuff is in fluid communication with the opening of the air cuff.

The air cuff tubing has a proximal end, a distal end, and an intermediate portion disposed between the proximal and distal ends of the air cuff. The tubing defines an interior, and the distal end of the air cuff tubing is sealingly coupled to the second opening of the slider cuff such that the interior of the air cuff tubing is in fluid communication with the channel of the slider cuff. At least a portion of the intermediate portion of the air cuff tubing is slidably disposed adjacent the exterior surface of the endotracheal tube in a direction parallel to the tube axis.

The pointer is coupled to the intermediate portion of the air cuff tubing and is disposed in a first axial position relative to the visual indicator portion when the distal end of the endotracheal tube is in an acceptable position within the trachea.

When axial movement of the slider cuff occurs, the movement of the slider cuff causes movement of the pointer in a direction that is parallel to the tube and slider cuff axes such that the pointer is in a second position that is spaced apart from the first position.

Figure 1:
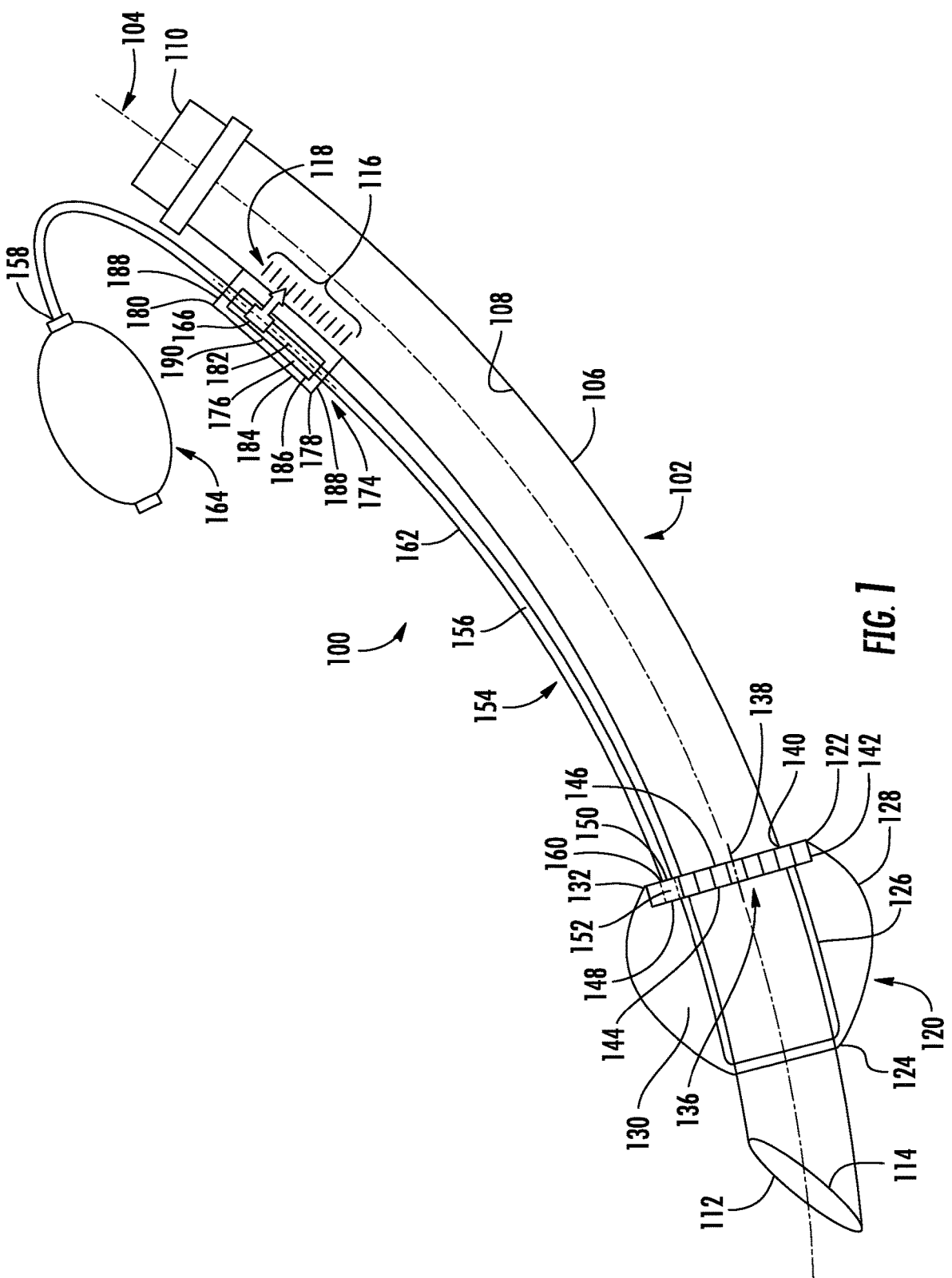
FIG. 1 is a perspective view of an endotracheal tube assembly in accordance with one implementation.

FIG. 1 shows one implementation of endotracheal tube assembly 100 with an endotracheal tube 102, an inflatable annular air cuff 120, an annular slider cuff 136, an air cuff tubing 154, an air cuff tubing guide 174, and a pointer 166. The endotracheal tube 102 has a tube axis 104, an exterior surface 106, an interior surface 108, a proximal end 110, and a distal end 112. The distal end 112 of the endotracheal tube 102 is designed for insertion into the trachea of a patient such that the endotracheal tube 102 extends out of the mouth of the patient with the proximal end 110 of the endotracheal tube 102 being disposed external to the patient. For example, the distal end 112 of the endotracheal tube shown in FIG. 1 has a curved, atraumatic edge 114, which is designed for easier insertion into the trachea. While the endotracheal tube 102 shown in FIG. 1 has a circular cross-section, the cross-section of the endotracheal tube in other implementations can be any shape suitable for insertion into the trachea of a patient, for example, an oval, triangle, rectangle, or other polygonal shape. The cross-section of the tube 102 is viewed through a plane that extends orthogonal to the central axis of the tube 102.

The endotracheal tube 102 also includes a visual indicator portion 116 adjacent the proximal end 110 of the endotracheal tube 102. The visual indicator portion 116 of the endotracheal tube 102 shown in FIG. 1 is a plurality of measurement markings 118 located along the exterior surface 106 of the endotracheal tube 102. The markings 118 are spaced apart equidistant as measured in a direction that is parallel to the tube axis 104. However, in some implementations, the visual indicator portion can be any indicator that is viewable from the exterior of the endotracheal tube 102, for example, ink lines, one or more opaque areas, indentations, or raised portions. While the visual indicator portion 116 of FIG. 1 is disposed on the exterior surface 106 of the endotracheal tube 102, in other implementations, the visual indicator portion can be disposed on an interior surface 108 of the endotracheal tube 102 or incorporated in the material of the endotracheal tube 102. In addition, the endotracheal tube 102 in FIG. 1 is translucent, but in other implementations, the tube is opaque.

The inflatable annular air cuff 120 has a proximal end 122, a distal end 124, an inner annular wall 126, and an outer annular wall 128. The inner annular wall 126 and outer annular wall 128 extend between the proximal end 122 and distal end 124 of the air cuff 120 and define an interior 130 of the air cuff 120. As seen in FIG. 1, the air cuff 120 is disposed around the exterior surface 106 of the endotracheal tube 102. The distal end 124 of the air cuff 120 is closer than the proximal end 122 of the air cuff 120 to the distal end 112 of the endotracheal tube 102. The distal end 124 of the air cuff 120 is affixed to the endotracheal tube 102, and the proximal end 122 of the air cuff 120 defines an opening 132 between the inner annular wall 126 and outer annular wall 128. The distal end 124 of the air cuff 120 in FIG. 1 is affixed to the endotracheal tube 102 by an adhesive, but in other implementations, the distal end of the air cuff is integrally formed with the endotracheal tube or is affixed to the endotracheal tube by any other suitable fastening means, for example, fasteners, welding, interference fit, or male/female connectors. While the air cuff 120 shown in FIG. 1 has an annular shape, the air cuff in other implementations can be multiple inflatable segments spaced circumferentially around the exterior surface of the endotracheal tube, each segment having its own opening between its inner wall and outer wall.

The slider cuff 136 has an annular shape with a slider axis 138, an inner wall 140 and an outer wall 142 that are opposite and spaced apart from each other, and a first side 144 and a second side 146 extending between the inner wall 140 and outer wall 142 and opposite and spaced from each other. The first side 144 of the slider cuff 136 defines a first opening 148, and the second side 146 of the slider cuff 136 defines a second opening 150. A channel 152 extends between the first opening 148 and second opening 150 through the slider cuff 136. The slider cuff 136 is slidably disposed around the exterior surface 106 of the endotracheal tube 102 such that the inner wall 140 of the slider cuff 136 is adjacent the exterior surface 106 of the endotracheal tube 102 and the slider axis 138 is coaxial with the tube axis 104. The slider cuff 136 is affixed to the proximal end 122 of the air cuff 120 such that the first opening 148 of the slider cuff 136 is in fluid communication with the opening 132 of the air cuff 120. The slider cuff 136 in FIG. 1 is affixed to the air cuff 120 by an adhesive, but in other implementations, the slider cuff is integrally formed with the air cuff or is affixed to the air cuff by any other suitable fastening means, for example, fasteners, welding, interference fit, or male/female connectors. While the slider cuff 136 shown in FIG. 1 has a circular cross-section, the cross-section of the slider cuff in other implementations can be any suitable shape that allows the slider cuff to be slidably disposed around the endotracheal tube, for example, oval, triangle, rectangle, or other polygonal shape. The cross-section of the slider cuff 120 is viewed through a plane that extends orthogonal to the central axis of the slider cuff 120.

The air cuff tubing 154 has an interior 156, a proximal end 158, a distal end 160, and an intermediate portion 162 that is disposed between the proximal end 158 and distal end 160 of the air cuff tubing 154. The distal end 160 of the air cuff tubing 154 is sealingly coupled to the second opening 150 of the slider cuff 136 such that the interior 156 of the air cuff tubing 154 is in fluid communication with the channel 152 of the slider cuff 136. Thus, the opening 132 of the air cuff 120, is also in fluid communication with the interior 156 of the air cuff tubing 154 by way of the slider cuff channel 152. The distal end 160 of the air cuff tubing 154 in FIG. 1 is coupled to the slider cuff 136 by an adhesive, but in other implementations, the air cuff tubing is integrally formed with the slider cuff or is affixed to the slider cuff by any other fastening suitable means, for example, fasteners, welding, interference fit, or male/female connectors. At least a portion of the intermediate portion 162 of the air cuff tubing 154 is slidably disposed adjacent the exterior surface 106 of the endotracheal tube 102 in a direction parallel to the tube axis 104. The proximal end 158 of the air cuff tubing 154 is coupled with an air cuff pilot balloon 164 such that the interior of the air cuff pilot balloon 164 is in fluid communication with the interior 156 of the air cuff tubing 154. The body of the air cuff pilot balloon 164 is made from a resilient material that is biased toward an inflated position. The air cuff pilot balloon 164 includes a one-way valve such that forcing the body of the air cuff pilot balloon 164 toward a collapsed position pumps air into the interior 130 of the air cuff 120 via the air cuff tubing 154 and slider cuff channel 152. The one-way valve prevents the backflow of air from the interior 130 of the air cuff 120 such that the air cuff 120 remains inflated.

The pointer 166 is coupled to the intermediate portion 162 of the air cuff tubing 154. When the distal end 112 of the endotracheal tube 102 is in an acceptable position within the trachea, the pointer 166 is disposed in a first axial position relative to the visual indicator portion 116. The pointer 166 in FIG. 1 is an arrow pointing toward the visual indicator portion 116, but in other implementations, the pointer could be any shape or marking suitable to visually indicate a change in the position of the pointer with respect to the visual indicator portion (e.g., a line, a dot, or an area)

When the endotracheal tube assembly 100 is used in a procedure, the distal end 112 of the endotracheal tube 102 is inserted into the trachea of a patient. Once the distal end 112 of the endotracheal tube 102 is in an acceptable position, the air cuff 120 is inflated such that the outer annular wall 128 of the air cuff 120 contacts the trachea. The contact between the outer annular wall 128 of the air cuff 120 and the trachea maintains the position of the air cuff 120 position within the trachea during the procedure. Because the air cuff 120 is affixed to the pointer 166 via the slider cuff 136 and air cuff tubing 154, axial movement of the slider cuff 136 with respect to the endotracheal tube 102 causes movement of the pointer 166 in a direction parallel to the endotracheal tube axis 104 and slider cuff axis 138. Because the visual indicator portion 116 is disposed on the endotracheal tube 102, the movement of the slider cuff 136 causes the pointer 166 to move to a second axial position relative to the visual indicator portion 116. Thus, an operator of the endotracheal tube assembly 100 observing that the pointer 166 has moved from the first axial position to a second axial position with respect to the visual indicator portion 116 would be able to determine that the distal end 112 of the endotracheal tube 102 has moved from the acceptable position within the trachea.

The endotracheal tube assembly 100 of FIG. 1 also includes an air cuff tubing guide 174. The air cuff tubing guide 174 includes a channel 176 that extends between a first end 178 and a second end 180 of the air cuff tubing guide 174. The first end 178 and second end 180 are axially spaced apart along a central axis 182 of the air cuff tubing guide 174. An external surface 184 of the air cuff tubing guide 174 is coupled to the exterior surface 106 of the endotracheal tube 102, and the central axis 182 of the air cuff tubing guide 174 extends parallel to the tube axis 104. The air cuff tubing 154 extends through the air cuff tubing guide channel 176 and openings 188 defined by the first end 178 and second end 180 of the air cuff tubing guide 174. The air cuff tubing guide 174 defines a slot 190 extending between the external surface 184 and an internal surface 186 of the air cuff tubing guide 174, and the pointer 166 extends from the air cuff tubing 154 through the slot 190.

Figure 2:
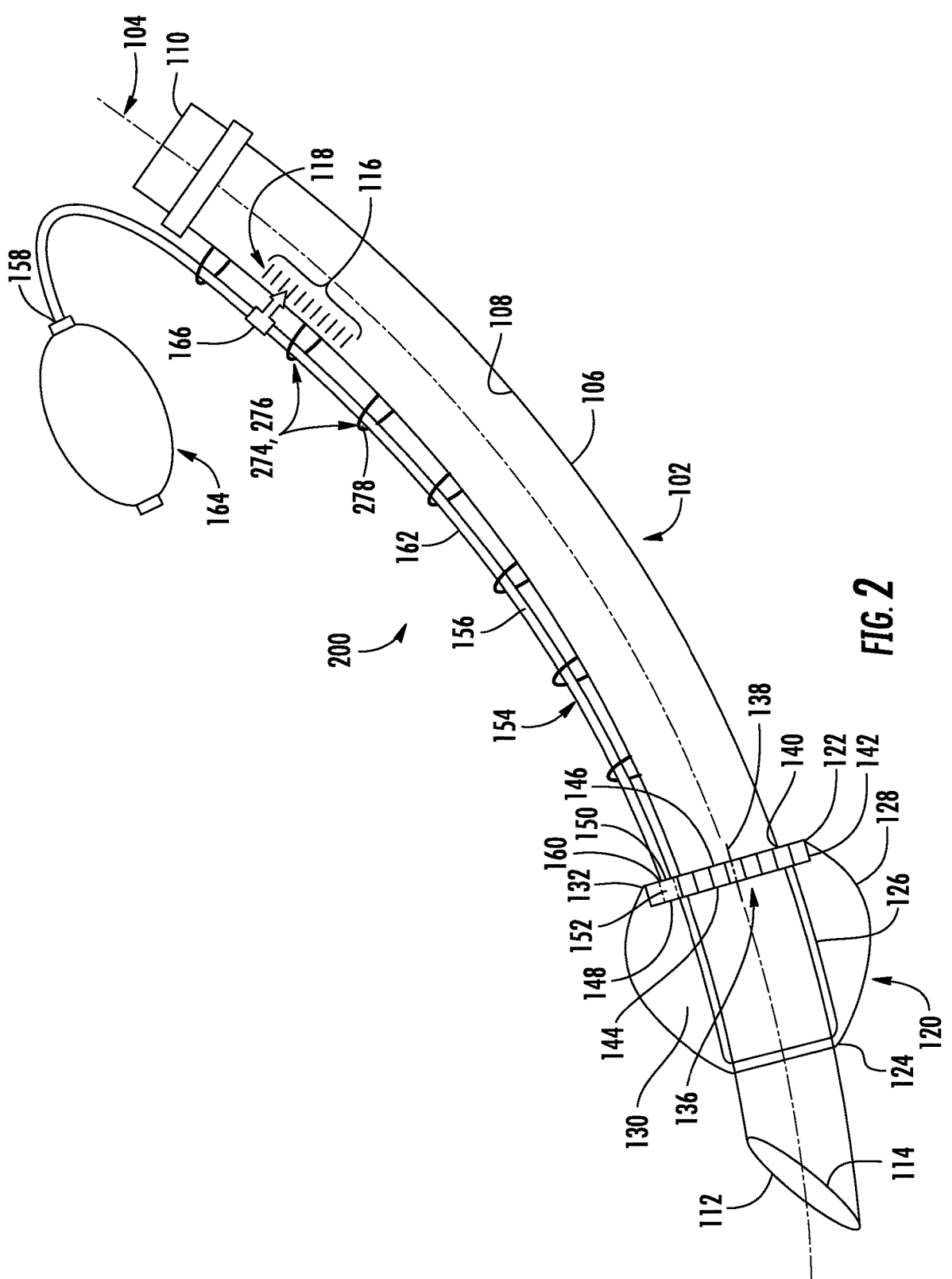
FIG. 2 is a perspective view of an endotracheal tube assembly according to another implementation.

The endotracheal tube assembly 200 of FIG. 2 is similar to the endotracheal tube assembly 100 of FIG. 1, but the endotracheal tube assembly 200 of FIG. 2 includes a different implementation of the air cuff tubing guide 274. In FIG. 2, the air cuff tubing guide 274 includes a plurality of loops 276 that are coupled to the exterior surface 106 of the endotracheal tube 102. Each loop 276 defines an opening 278, and the air cuff tubing 154 extends through the loop openings 278. The pointer 166 coupled to the air cuff tubing 154 is axially spaced apart from the loops 276 such that the loops 276 do not interfere with the axial movement of the pointer 166 as the pointer 166 moves from the first position to the second position, and vice versa.

A number of implementations have been described. Nevertheless, it will be understood that various modifications may be made without departing from the spirit and scope of the claims. Accordingly, other implementations are within the scope of the following claims.

Certain terminology is used herein for convenience only and is not to be taken as a limitation on the present claims. In the drawings, the same reference numbers are employed for designating the same elements throughout the several figures. A number of examples are provided, nevertheless, it will be understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

What is claimed is:

1. An endotracheal tube assembly comprising:
   an endotracheal tube having a tube axis, an exterior surface, a proximal end, and a distal end for inserting into a trachea, the tube further comprising a visual indicator portion viewable from the exterior surface, the visual indicator portion being adjacent the proximal end of the endotracheal tube;
   an inflatable annular air cuff having a proximal end, a distal end, and inner and outer annular walls that extend between the proximal and distal ends and define an interior of the inflatable air cuff, wherein the air cuff is disposed around the exterior surface of the endotracheal tube such that the distal end of the air cuff is closer than the proximal end of the air cuff to the distal end of the endotracheal tube, the distal end of the air cuff being affixed to the endotracheal tube and the proximal end of the air cuff defining an opening between the inner and outer annular walls;

an annular slider cuff having a slider axis, the slider cuff defining a first opening, a second opening, and a channel that extends between the first and second openings through the slider cuff, wherein the slider cuff is slidably disposed around the exterior surface of the endotracheal tube such that the slider axis is coaxial with the tube axis, the slider cuff being affixed to the proximal end of the air cuff such that the first opening of the slider cuff is in fluid communication with the opening of the air cuff;

an air cuff tubing having a proximal end, a distal end, and an intermediate portion disposed between the proximal and distal ends of the air cuff, the tubing defining an interior, the distal end of the air cuff tubing being sealingly coupled to the second opening of the slider cuff such that the interior of the air cuff tubing is in fluid communication with the channel of the slider cuff, wherein at least a portion of the intermediate portion of the air cuff tubing is slidably disposed adjacent the exterior surface of the endotracheal tube in a direction parallel to the tube axis; and a pointer coupled to the intermediate portion of the air cuff tubing and maintained a fixed distance from the slider cuff, the pointer being disposed in a first axial position relative to the visual indicator portion when the distal end of the endotracheal tube is in an acceptable position within the trachea, wherein axial movement of the slider cuff relative to the endotracheal tube, when the distal end of the endotracheal tube is in an acceptable position within the trachea, causes movement of the pointer in a direction that is parallel to the tube axis such that the pointer is in a second axial position that is spaced apart from the first axial position.

2. The endotracheal tube assembly of claim 1, wherein the visual indicator portion comprises a plurality of measurement markings disposed in a pattern parallel to the tube axis.

3. The endotracheal tube assembly of claim 2, wherein the measurement markings are disposed on the exterior surface of the tube.

4. The endotracheal tube assembly of claim 1, wherein the distal end of the air cuff is affixed to the endotracheal tube by an adhesive.

5. The endotracheal tube assembly of claim 1, further comprising an air cuff tubing guide defining a channel that extends between a first end and a second end of the air cuff tubing guide, the ends being axially spaced apart along a central axis of the air cuff tubing guide, an external surface of the air cuff tubing guide being coupled to the exterior surface of the endotracheal tube, wherein the central axis of the air cuff tubing guide extends parallel to the tube axis, the air cuff tubing extends through the channel and openings defined by the first and second ends of the air cuff tubing guide.

6. The endotracheal tube assembly of claim 5, wherein the air cuff tubing guide defines a slot extending between an external surface and an internal surface of the air cuff tubing guide, the pointer extending from the air cuff tubing through the slot.

7. The endotracheal tube assembly of claim 5, wherein the air cuff tubing guide comprises a plurality of loops coupled to the exterior surface of the endotracheal tube, wherein the pointer coupled to the air cuff tubing is axially spaced apart from the loops.

8. The endotracheal tube assembly of claim 1, wherein the distal end of the endotracheal tube comprises a curved, atraumatic edge.

9. The endotracheal tube assembly of claim 1, wherein the proximal end of the air cuff tubing is coupled with an air cuff pilot balloon.

10. An endotracheal tube assembly comprising:

an endotracheal tube including a plurality of spaced apart indicator markings;

an inflatable annular air cuff disposed around the endotracheal tube;

a slider cuff slidably disposed around the endotracheal tube and affixed to the air cuff;

an air cuff tubing in fluid communication with the inflatable annular air cuff via the slider cuff, and slidably disposed relative to the endotracheal tube; and a pointer coupled to the air cuff tubing and movable therewith relative to the endotracheal tube, wherein the pointer is disposed in a first axial position relative to the plurality of spaced apart indicator markings when the slider cuff and the air cuff tubing are arranged in a first position within a trachea, and wherein a distance between the pointer and the slider cuff is fixed so that axial movement of the slider cuff, when a distal end of the endotracheal tube is in the first position within the trachea, causes movement of the pointer relative to the plurality of spaced apart indicator markings to a second position that is spaced apart from the first position.

11. The endotracheal tube assembly of claim 10, wherein the air cuff is affixed to the endotracheal tube by an adhesive.

12. The endotracheal tube assembly of claim 10, further comprising an air cuff tubing guide defining a channel coupled to the endotracheal tube, wherein the air cuff tubing extends through the channel.

13. The endotracheal tube assembly of claim 12, wherein the air cuff tubing guide defines a slot sized to receive the pointer, and wherein the pointer extends through the slot.

14. The endotracheal tube assembly of claim 12, wherein the air cuff tubing guide includes a plurality of loops coupled to the endotracheal tube, and wherein the pointer is coupled to the air cuff tubing spaced apart from the plurality of loops.

15. The endotracheal tube assembly of claim 10, wherein the endotracheal tube comprises a curved, atraumatic edge.

16. The endotracheal tube assembly of claim 10, wherein the air cuff tubing is coupled with an air cuff pilot balloon.

17. An endotracheal tube assembly comprising:

an endotracheal tube including a plurality of spaced apart indicator markings;

an inflatable annular air cuff disposed around the endotracheal tube;

a slider cuff slidably disposed around the endotracheal tube and affixed to the air cuff;

an air cuff tubing in fluid communication with the inflatable annular air cuff via the slider cuff, and slidably disposed relative to the endotracheal tube; and a pointer coupled to the air cuff tubing in a fixed relationship with the slider cuff, wherein the endotracheal tube assembly defines a first position relative to the slider cuff and is arranged desirably with a trachea, and wherein movement of the endotracheal tube relative to the slider cuff, when a distal end of the endotracheal tube is in the first position within the trachea, causes movement of the pointer relative to the plurality of spaced apart indicator markings to indicate that the endotracheal tube has moved away from the first position.

18. The endotracheal tube assembly of claim 17, wherein the air cuff is affixed to the endotracheal tube by an adhesive.

19. The endotracheal tube assembly of claim 17, further comprising an air cuff tubing guide defining a channel coupled to the endotracheal tube, wherein the air cuff tubing extends through the channel, wherein the air cuff tubing guide defines a slot sized to receive the pointer, and wherein the pointer extends through the slot.

20. The endotracheal tube assembly of claim 17, further comprising an air cuff tubing guide including a plurality of loops coupled to the endotracheal tube, and wherein the pointer is coupled to the air cuff tubing spaced apart from the plurality of loops.

\* \* \* \* \*